US012681025B2

(12) United States Patent
Onundarson et al.

(10) Patent No.: US 12,681,025 B2
(45) Date of Patent: ***Jul. 14, 2026

(54) METHOD AND KIT FOR MONITORING ANTICOAGULANT THERAPY

(71) Applicant: FIIX DIAGNOSTICS, Gardabaer (IS)

(72) Inventors: Pall T. Onundarson, Gardabaer (IS); Brynja R. Gudmundsdottir, Reykjavik (IS)

(73) Assignee: FIIX DIAGNOSTICS, Gardabaer (IS)

( * ) Notice: Subject to any disclaimer, the term of this patent is extended or adjusted under 35 U.S.C. 154(b) by 0 days.

This patent is subject to a terminal disclaimer.

(21) Appl. No.: 19/288,053

(22) Filed: Aug. 1, 2025

(65) Prior Publication Data

US 2025/0355004 A1 Nov. 20, 2025

Related U.S. Application Data

(63) Continuation of application No. 18/823,356, filed on Sep. 3, 2024, now Pat. No. 12,405,281.

(60) Provisional application No. 63/683,855, filed on Aug. 16, 2024, provisional application No. 63/560,939, filed on Mar. 4, 2024.

(51) Int. Cl.
*G01N 33/86* (2006.01)

(52) U.S. Cl.
CPC ... *G01N 33/86* (2013.01); *G01N 2333/96463* (2013.01)

(58) Field of Classification Search
CPC . G01N 33/86; G01N 2333/96463; C12Q 1/56
See application file for complete search history.

(56) References Cited

U.S. PATENT DOCUMENTS

| | | |
|---|---|---|
| 3,947,378 A | 3/1976 | Babson |
| 9,234,902 B2 | 1/2016 | Onundarson et al. |

OTHER PUBLICATIONS

Haraldsson Magnus H. et al., "Performance of Prothrombin-Proconvertin Time as a Monitoring Test of Oral Anticoagulation Therapy", Am J Clin Pathol., Jun. 1, 1997, pp. 672-680.
International Search Report from corresponding PCT Application No. PCT/IB2025/050980, May 16, 2025.
Allington, "Owren's Method for the Control of Anticoagulant Therapy", Journal of Clinical Pathology, as early as Oct. 31, 1957, pp. 62-68, vol. 11, No. 62.
Gudmundsdottir et al., "Critical role of factors II and X during coumarin anticoagulation and their combined measurement with a new Fiix-prothrombin time", Thrombosis Research, as early as Oct. 1, 2012, pp. 674-681, vol. 130, Issue 4.
Jonsson et al., "During warfarin induction, the Fiix-prothrombin time reflects the anticoagulation level better than the standard prothrombin time", Journal of Thrombosis and Haemostasis, as early as Jan. 1, 2017, pp. 131-139, vol. 15, Issue 1.
Onundarson et al., "Fiix-prothrombin time versus standard prothrombin time for monitoring of warfarin anticoagulation: a single centre, double-blind, randomised, non-inferiority trial", The Lancet Haematology, as early as Jun. 1, 2015, pp. e231-e240, vol. 2, Issue 6.
Onundarson et al., "Replacement of traditional prothrombin time monitoring with the new Fiix prothrombin time increases the efficacy of warfarin without increasing bleeding. A review article", Thrombosis Journal, Oct. 15, 2021, pp. 1-10, vol. 19, No. 72.
Oskarsdottir et al., "Ignoring instead of chasing after coagulation factor VII during warfarin management: an interrupted time series study", Blood, May 20, 2021, pp. 2745-2755, vol. 137, No. 20.
Owren et al., "The control of dicumarol therapy and the quantitative determination of prothrombin and proconvertin", Scandinavian Journal of Clinical and Laboratory Investigation, as early as Jul. 30, 1951, pp. 201-208, vol. 3, Issue 3.
Quick et al., "A study of the coagulation defect in hemophilia and in jaundice", J Bio Chem, as early as Apr. 1, 1935, pp. 501-511.
Xi et al., "The relative importance of the factors II, VII, IX and X for the prothrombinase activity in plasma of orally anticoagulated patients", Thrombosis and Haemostasis, Sep. 29, 1989, 5 pages.
Zivelin et al., "Mechanism of the anticoagulant effect of warfarin as evaluated in rabbits by selective depression of individual procoagulant vitamin K-dependent clotting factors", The Journal of Clinical Investigation, as early as Nov. 1, 1993, pp. 2131-2140, vol. 92.

*Primary Examiner* — Lynn Y Fan
(74) *Attorney, Agent, or Firm* — Workman Nydegger

(57) ABSTRACT

A method and kit are provided for measuring and monitoring a combined effect of an anticoagulant drug on coagulation factors II and X in a patient taking the anticoagulant drug. The method includes adding one or more coagulation reagents with the factor VII to a test sample and determining blood clotability of the test sample by measuring an influence of factors II and X.

11 Claims, 4 Drawing Sheets

XY: Normalized ratios in FVII deficient plasma; thromplastin +/- plasma reagents

Purified factor VII (pFVII) added to thromboplastin(TP)

METHOD AND KIT FOR MONITORING ANTICOAGULANT THERAPY

FIELD OF INVENTION

The present disclosure concerns medical diagnosis and drug monitoring, specifically the field of measuring blood coagulation in patients taking pharmaceutical compounds for anticoagulation therapy.

BACKGROUND

Blood clotting is the mechanism that prevents continuing blood loss when any part of the blood circulation system is injured. Clotting involves the formation of a semi-solid mass of blood material, which acts to plug vessel wounds. The blood circulation system comprises a series of interacting components in the blood and vessel wall that must remain in balance. An inactive system response causes a risk of severe and fatal bleeding. In contrast, excessive activity of the blood clotting response mechanism causes a risk of blood clot formation (i.e., thrombosis and thromboembolism) within the circulatory system, clogging arteries, with potentially fatal consequences due to tissue necrosis (cell death).

Anticoagulants or "blood thinners" are among the most frequently administered drug classes, and within this class, vitamin K antagonists (VKA, coumarins) are distinctive agents that can be administered orally. Due to the delicate balance of the blood clotting system and the variation in patient sensitivity and responsiveness to the therapy, VKA doses should be carefully adjusted and regularly monitored because the patient response and suitable dose requirements frequently change with time.

The blood coagulation system comprises a complex system of interlinked proenzymes, enzymes, and cofactors that each contribute to blood clotting on the surface of activated platelets and endothelial cells and in ruptured vessels in the human body. When the system is activated, e.g., in a vessel wound, the ultimate result is the formation of a blood clot containing an insoluble fibrin mesh. In the body, the coagulation process is carefully controlled on the surface of activated platelets and endothelial cells. Still, in the testing laboratory, the platelet surface is usually substituted with suitable phospholipids. The proenzymes, enzymes and cofactors are traditionally named coagulation factors (F).

Four coagulation factors, i.e., FII, FVII, FIX and FX, that are formed in the liver, are inactive unless they become further carboxylated by a vitamin K dependent enzyme process following synthesis in the liver. In patients deficient in vitamin K or treated with a VKA, the amount of carboxylated vitamin K dependent (VKD) factors is reduced and, hence, the blood clotting ability (i.e., coagulability) of the relevant patient's blood. Unless the effect of VKA is controlled, this may lead to severe and even fatal internal hemorrhaging. But by reducing the VKD factor levels in a controlled manner, abnormal blood clotting within the vessels (thrombosis) can be prevented while also minimizing the risk of bleeding. It is therefore imperative that the effect of VKA be monitored with appropriate coagulation tests. Due to the variable sensitivity of patients to VKA action the VKA drug dose must also be individualized based on monitoring. Based on test results, the dose can then be adjusted, maximizing the antithrombotic effect while minimizing the risk of abnormal bleeding caused by over-anticoagulation.

The monitoring of blood clotting activity in VKA patients has historically, i.e., for over seventy years, been based on measuring the prothrombin time (PT), either as the original Quick P T (Quick, A., *J Bio Chem* 1935 (109): p. 73-4) or as it's modification, the Owren's PT (also known as PP, P&P-test, or prothrombin complex test) (Owren and Aas. *Scand J Clin Lab Invest,* 1951. 3(3): p. 201-8.). The Quick P T test measures the clotting activity of three out of four vitamin K dependent clotting factors (i.e., FII, FVII, and FX) as well as that of fibrinogen (factor I) and factor V in a blood plasma sample which has been depleted from calcium, by adding a coagulation reagent (thromboplastin, tissue factor) and calcium, and subsequently measuring the time that it takes the blood to coagulate. The latter test (P&P) is a modification of the Quick P T, where adsorbed plasma (totally deficient in the four vitamin K dependent factors; II, VII, IX and X) is mixed into the test plasma, correcting for any possible deficiency of factor V or fibrinogen and leaving the P&P test only sensitive to factors II, VII and X. Hence, the Quick-PT test is also sensitive to deficiency of factors V and fibrinogen, which are not vitamin K dependent and, if deficient, may confound results in patients taking VKA. With both tests, however, the measured clotting time is equally sensitive to a reduction in any of the three vitamin K dependent factors that both the tests measure, i.e., FII, FVII and FX. FIX coagulant activity is not measured by these tests. The clotting times obtained with the Quick PT based tests have in practice been presumed to directly reflect the antithrombotic effect of VKA in patients except during initiation of VKA therapy. However, this may not always be the case.

Although conventional warfarin monitoring using the PT is identically sensitive to reductions in any of FII, VII and FX (Gudmundsdottir B R et al, *Thromb Res.* 2012; 130 (4): 674-81), experimental evidence, including that of the inventors of the present disclosure, has suggested that that the antithrombotic effect of VKA drugs mainly relies on reducing FII and FX but not that of FVII. (Gudmundsdottir B R et al, *Thromb Res.* 2012; 130 (4): 674-81; Jonsson P I et al, *J Thromb Haemost.* 2017; 15 (1): 131-9; Xi M et al, *Thromb Haemost.* 1989; 62:788-91; Zivelin A et al, *J Clin Invest.* 1993; 92:2131-40). Furthermore, rapid fluctuations in the PT during VKA therapy are mainly driven by changes that occur in FVII that has a very short half-life. The very short half-life of FVII (4-6 hours) leads to this particular factor having a major influence on the PT-INR in the short term, e.g., during initiation, after dose changes, and when dose changes are made repeatedly within short time intervals without reflecting the antithrombotic effect.

Therefore, considering whether warfarin stability could be improved by monitoring only the effect of VKA on FII and FX, the inventors discovered a method for warfarin monitoring, called the coagulation factor (F) II and X test (Fiix-test, also known as Fiix prothrombin time or Fiix-PT). With the Fiix test, test plasma is corrected by mixing it with a plasma reagent that has been depleted of factors II and factor X. The double immunodepleted plasma-based Fiix reagent method is described in U.S. Pat. No. 9,234,902 ("the '902 patent"). The plasma reagent corrects all coagulation factor deficiencies in the test plasma except those of factor II and factor X before adding a coagulation trigger such as thromboplastin to measure a clotting time. Fiix normalized ratio (Fiix-NR) is calculated in analogous fashion to PT-INR and by ignoring FVII reductions, less variable normalized ratio and less variable dosing is achieved. (Jonsson P I et al, *J Thromb Haemost.* 2017; 15 (1): 131-9; Onundarson P et al, *The Lancet Haematology.* 2015; 2 (6): e231-e40; Oskarsdottir A R et al, *Blood.* 2021; 137 (20): 2745-55). Furthermore, in the investigator initiated blinded mixed-population RCT, a 48% statistically non-inferior reduction in total thrombo-embolism (TE) without increased bleeding was found with Fiix-NR monitored warfarin (Fiix-warfarin) compared to conventional PT-warfarin. (Onundarson P et al, *The Lancet Haematology.* 2015; 2 (6): e231-e40) After publication of the results, in July 2016 we replaced PT-INR monitoring of warfarin with Fiix-monitoring. We then confirmed in a pre-post interrupted time series study that the benefit of Fiix-warfarin over PT-warfarin extends into clinical practice. (Oskarsdottir A R et al, *Blood.* 2021; 137 (20): 2745-55).

The main drawbacks of existing methods, particularly those using a plasma reagent only deficient in both factors II and X (e.g., the Fiix reagent method described in the '902 patent), relate to manufacturing cost and time. Specifically, resources needed to manufacture the Fiix deficient plasma reagent require double immunodepletion, i.e., chromatography using two separately manufactured and expensive antibodies to factor II and factor X in the chromatographic columns that bind the relevant factors and remove them from the filtered plasma. The number of steps to generate the deficient plasma reagent in existing methods therefore require a slow, methodical, and expensive approach.

SUMMARY

Given the above-mentioned prior art issues, the inventors of the present disclosure identified a need for an improved test to monitor anticoagulant therapy. The inventors developed a novel method using a new alternative reagent that supplies factor VII, but is still deficient in factors II and X. The alternative reagent can be used as a simplified deficient plasma reagent or mixed into the triggering agent such as thromboplastin for providing reliable results with reduced manufacturing costs. An alternative solution of the present disclosure provides a reagent plasma using adsorbed (e.g., with barium sulphate) plasma that has been made deficient in all vitamin K dependent factors and subsequently adding back factor VII in a sufficient quantity to correct the FVII final concentration in the reagent-test whole blood or plasma sample mixture to over 50% (0.5 u/mL). The reagent-test sample mixture remains deficient in FII, FX and FIX. In this manner, any influence of reduced FVII in test blood or plasma sample on clotting is eliminated when thromboplastin (tissue factor), and/or other reagents that directly activate coagulation factor X and do not activate FIX, are used to initiate the clotting reaction. The proposed method bypasses activation of coagulation factor IX and corrects factor VII to achieve the goal of measuring the simultaneous influence of FII and FX only on the clotting process. Alternatively, reagent plasma and factor VII can be mixed into the reagent activator, such as thromboplastin that is subsequently added to the patient test plasma or whole blood to measure the same anticoagulant effect (i.e., a measurement of reduced factors II and X only). In other words, the disclosed method for monitoring anticoagulant therapy measures the simultaneous influence of FII and FX while ignoring or omitting the influence of fibrinogen (FI), FV, and FVII on the clotting process. Thus, the method of the present disclosure provides reliable results at reduced manufacturing costs.

The present disclosure thus provides a method for measuring an effect of an anticoagulant drug in a patient, the effect being based on measuring, in a test plasma sample of the patient, the influence of the anticoagulant drug on the combined activity of only coagulation factors II and X. The test plasma sample is mixed with a plasma reagent that has been made deficient in only factors II, IX, and X to create a corrected plasma sample. One or more coagulation reagents that activate factor VII or X and calcium reagents are then added to the corrected plasma sample to initiate a blood clotting sequence. Subsequently, blood clotting ability of the corrected plasma sample is determined by measuring blood clotting time or thrombin generation. Alternatively, reagent plasma and factor VII can be mixed into the reagent activator, such as thromboplastin that is subsequently added to the patient test plasma or whole blood to measure the same anticoagulant effect (i.e., a measurement of reduced factors II and X only).

The present disclosure also relates to method for monitoring anticoagulant therapy by (1) combining adsorbed plasma with a solution containing factor VII to correct a final concentration of factor VII in a resulting sample mixture, the final concentration of factor VII being corrected to over 50% or greater than 0.5 u/mL, the resulting sample mixture being deficient in factors II, X and IX, (2) adding a coagulation reagent to the resulting sample mixture to initiate a clotting reaction, wherein the coagulation reagent directly or by forming a complex with activated factor VII (i.e., tissue factor, a component of thromboplastin) activates factor X and does not activate factor IX, (3), measuring simultaneous influence of factors II and X on the clotting reaction; and (4) determining blood clotting ability of the resulting sample mixture by measuring blood clotting time or thrombin generation. Based on the determined blood clotting ability, the dose of anticoagulant drug may be adjusted to reach a recommended therapeutic INR (international normalized ratio) of about 2 to about 3 (or other defined target), by either increasing the dose to maximize an antithrombotic effect of the anticoagulant drug or decreasing the dose to minimize risk of abnormal bleeding caused by over-anticoagulation. As noted above, the disclosed method can include the possibility of making corrections in the thromboplastin without using a separate deficient plasma step. In other words, the reagent plasma and factor VII can be mixed into the reagent activator, such as thromboplastin that is subsequently added to the patient test plasma or whole blood to measure the same anticoagulant effect (i.e., a measurement of reduced factors II and X only).

The present disclosure also provides a test kit for measuring the activity of an anticoagulant drug in a patient. The test kit includes a coagulation triggering reagent and a factor-deficient plasma that is deficient in vitamin K dependent factors II, IX and X. The factor-deficient plasma includes a sufficient amount of factor VII as noted above. In an embodiment, before reintroducing factor VII into the factor-deficient plasma, the factor-deficient plasma is prepared by adsorption, e.g., with barium sulphate or aluminum hydroxide which is a standard procedure. The coagulation reagent is configured to activate factor VII or factor X directly and does not activate factor IX. Like the aforementioned method, the disclosed kit may also include means for directly correcting concentrations in the thromboplastin without using a separate deficient plasma. In an embodiment, purified FVII is mixed into thromboplastin that has been premixed with adsorbed plasma, prior to adding the modified thromboplastin to the test sample. The modified reagent includes thromboplastin and bovine adsorbed plasma in the proportion of 1:1. By adding reagent plasma and FVII either to the test sample or to the triggering reagent (e.g., thromboplastin), a clotting time that reflects the activity of both (and only) factors II and X together can be obtained.

The disclosed method and kit are provided to bypass activation of FIX and correct FVII (as well as FI (fibrinogen) and FV) to measure the simultaneous influence of FII and FX on the clotting process.

These and other features, aspects, and advantages of the present disclosure will be better understood in the following description and appended claims.

DEFINITIONS

"Coagulation reagent" refers to a reagent that triggers the coagulation pathway in a blood or plasma sample, which leads to the conversion of prothrombin to thrombin and fibrinogen to fibrin.

"Combined activity" of factors II and X refers to measured effects due to activity of both factors II and X while the effect of one is not differentiated from the other.

"Factor-deficient plasma" generally refers to normal plasma that has been made deficient in factors II, X, and IX but has been reintroduced with factor VII in sufficient quantity to correct the factor VII final concentration in the resulting reagent-test whole blood or plasma sample mixture to over 50% (0.5 u/mL).

"Normal plasma" refers to plasma suitable for use as control, from normal healthy individuals, preferably and typically pooled from several individuals to normalize any interindividual variation in concentration of relevant factors.

"Special coagulation triggering reagent" refers to a reagent (e.g., thromboplastin) that is premixed with adsorbed plasma (i.e., as a source of all factors excluding factors II, VII, IX and X) that has been supplemented or replenished with purified factor VII to provide a FVII concentration of over 50% (0.5 u/mL) in the final reagent-plasma or whole blood test sample mixture.

"Test plasma," "test plasma sample," or "test blood" refers in this context to plasma or whole blood from a patient or subject for whom a blood clotting test is desired.

"Viscosity" refers to characteristics of specified material (s) determining a degree of gelation, such as the firmness or hardness of the material, and the degree to which the material resists flowing like a fluid.

DETAILED DESCRIPTION OF VARIOUS EMBODIMENTS

Figure 1:
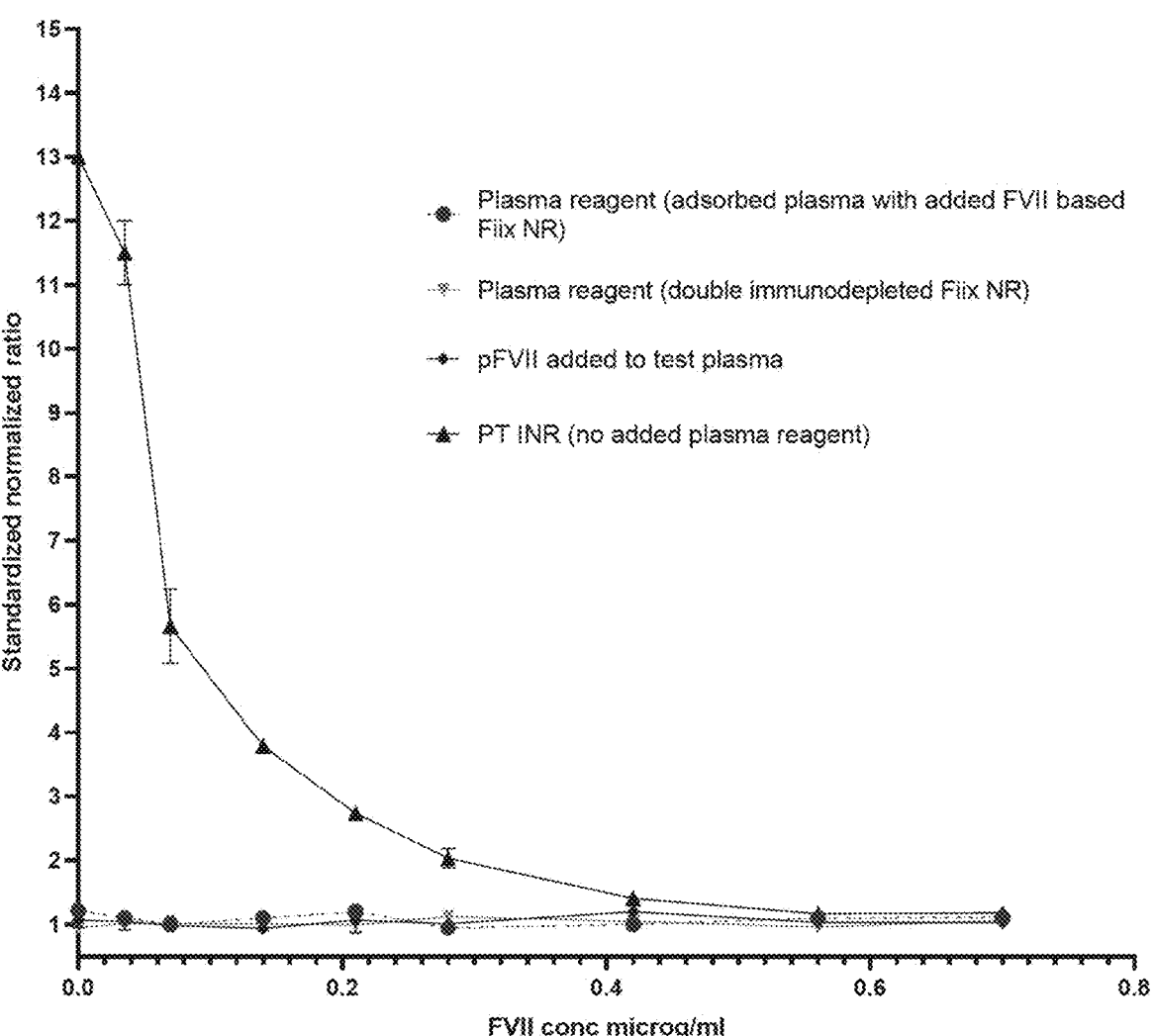
FIG. 1 is a graph illustrating expected normal ratio results using different methods in FVII deficient plasmas.

The present disclosure relates to a novel method, and corresponding kits based on the method, for determining blood clotting ability of test samples (e.g., human plasma or whole blood), particularly for measuring the activity of an anticoagulant drug in patients taking such drugs. The disclosed method eliminates the influence of coagulation factors other than factors II and X. The method improves anticoagulant therapy with coumarins (vitamin K antagonists, VKA), such as warfarin, which reduce the concentration of active (gamma-carboxylated) coagulation factors II, VII, IX and X. The new method may also have application to monitor other anticoagulants that inhibit factors II or X or both. The method differs from a standard prothrombin time (PT) test that is sensitive to reduced vitamin K dependent factor VII in addition to vitamin K dependent factors, II and X, and including two factors that are not affected by the drugs, i.e., fibrinogen (FI) and factor V.

The method of the present disclosure is based on measuring the combined activity of only coagulation factors II and X, meaning that the effects from other factors that may be variable in the test sample (e.g., factors I, V, and VII) are eliminated.

In an embodiment, the test sample is mixed with plasma deficient in factors II, X, and IX, i.e., adsorbed plasma or factor-deficient plasma, wherein the factor-deficient plasma includes factor VII in sufficient quantity to correct the factor VII final concentration in the reagent-test whole blood or plasma sample mixture to over 50% (0.5 u/mL). The ratio of the test plasma to the deficient plasma is suitably in the range from 1:1 to 1:20, preferably in the range 1:2 to 1:5, including but not limited to 1:2.5, 1:3, 1:3.5, 1:4, or 1:4.5. As used herein, the notation 1:2 means one part test plasma against two parts deficient plasma, i.e., three parts plasma in total (i.e., 33.3% test plasma and 66.7% deficient plasma). Alternatively, adsorbed plasma with added FVII is mixed into the thromboplastin before adding to the test sample to measure the same anticoagulant effect (i.e., a measurement of reduced factors II and X only).

In an embodiment, the plasma test sample is treated as for conventional coagulation tests, i.e., a fresh blood sample drawn from the patient is treated with citrate for calcium depletion, and red blood cells are separated from the plasma by centrifugation. The prepared test plasma sample can then conveniently be mixed with the deficient plasma, suitably before analysis or in automated instruments. The plasma test sample may be diluted in an embodiment with a buffer or saline solution. In a further embodiment the test sample may be whole blood.

A coagulation reagent that activates coagulation factor VII or factor X but not factor IX is added to the test plasma, along with a calcium reagent, to trigger coagulation. Other than platelet activation, calcium ions play a role in the activation of several coagulation factors. The coagulation reagent and calcium reagent can be pre-mixed together or each added separately to the test plasma sample. Alternatively, either or both reagents can be pre-mixed with the deficient plasma before adding calcium. Accordingly, the steps of the disclosed method involve mixing test plasma sample with deficient plasma and adding the coagulation reagent and calcium can be performed in one, two or three steps. In an embodiment, the coagulation reagent is diluted with water, a saline aqueous solution, or buffered aqueous solution. One skilled in the art will recognize that calcium reagents may not be required in test samples containing fresh whole blood. Thus, the use and type of calcium reagents used in the proposed solutions depends on the type of test sample (e.g., plasma sample versus fresh whole blood).

The coagulation reagent can be any commonly used reagents in conventional tests that directly, or through complex formation with activated factor VIIa, activates coagulation factor X without activating factor IX. Examples of the coagulation reagent used according to the present disclosure include thromboplastin (including recombinant tissue factor), factor VIIa, and exogenous activators, such as snake venom that activates factor X.

The present method works with activation of coagulation through the extrinsic pathway (high concentration tissue factor activation of FVII that subsequently activates factor X) or by directly activating factor X. Exogenous activators, such as snake venoms, can be used in the method of the present disclosure. Such venoms include Russell's viper venom (snake venom from Daboia russellii), which can be obtained from natural source or recombinantly produced. Other snake venoms which activate factor X directly, through the common pathway may also be used.

Thromboplastin is not a pure protein, but rather a complex of tissue factor protein and phospholipids. Tissue factor (also referred to as platelet tissue factor, factor III, thrombokinase or CD142) is an integral transmembrane protein that is a cell surface receptor for factor VIIa, functioning as a cofactor mandatory for the proteolytic activity of factor VIIa towards factor X converting factor X to the active protease factor Xa. According to an embodiment of the present disclosure, the tissue factor is associated with coagulant phospholipids for the full expression of its cofactor function.

Thromboplastin used in the disclosed method and kits can be obtained from animal sources, including but not limited to rabbit brain, human placenta, human brain, bovine brain, bovine lung, or other suitable sources. Thromboplastin can also be recombinantly produced thromboplastin, preferably recombinant human thromboplastin. Recombinant thromboplastin can be produced by expressing the tissue factor component in suitable cell culture, e.g., placental mouse cell culture, hamster ovary cells (CHO cells); fungal cells, prokaryotic organisms, e.g., in E. coli cultures; transgenic plants or other suitable expression vehicle, and subsequently the tissue factor is lipidated in vitro.

The calcium reagent source is generally but not necessarily calcium chloride. The amount/concentration of coagulation reagent in the method is generally similar to current methods for measuring coagulation. Calcium is used in a conventional concentration, such as in the range 1.0-4.0 mM, preferably 2.5 mM.

When thromboplastin is used, the results can be normalized based on an ISI value to provide a normalized ratio.

The coagulation reagent and/or deficient plasma are preferably lyophilized and in such case are reconstituted prior to use in water or suitable buffer.

Based on the disclosed method for measuring the effect of an anticoagulant drug in a patient, the dose of anticoagulant drug may be adjusted to reach a recommended therapeutic INR of about 2 to about 3 (or other target range), by either increasing the dose to maximize the antithrombotic effect of the anticoagulant drug or decreasing the dose to minimize risk of abnormal bleeding caused by over-anticoagulation.

In an embodiment, a method for measuring the simultaneous effect of an anticoagulant drug on coagulation factors II and X alone includes the step of mixing the test plasma with a source of coagulation factor VII in order to prevent influence of factor VII on test results. The source of factor VII can be a plasma reagent made deficient in only factors II, IX, and X but not in factor VII to create a corrected mixed plasma sample, or by adding excess coagulation factor VII to the test sample or triggering agent.

In an embodiment, a whole blood or plasma test sample from a patient anticoagulated with a vitamin K antagonist is mixed with a solution containing purified factor VII in a concentration sufficient to provide the mix with a final activity of over 50% (>0.5 u/mL). The whole common pathway of coagulation, namely factors I (fibrinogen), II, V and X but not VII, is measured. In samples from patients taking VKA anticoagulants, such as warfarin, the combined effect of FII and X is monitored because fibrinogen and factor V are not affected by the VKA action and thus remain stable in fresh samples from VKA-treated patients. This method is preferably administered when levels of fibrinogen and/or factor V are not deficient.

Endpoint Determination

The endpoint determination in the disclosed method includes but is not limited to manual (visual) determination by tilt-tube technique, mechanical detection using methods of clot detection such as "rolling ball" or vibrating probe technique (detecting when probe is static due to higher viscosity), optical detection methods using optical detection of fibrin formation, and also chromogenic techniques based on the use of chromogenic substrates, including substrates for thrombin (e.g. substrate S2238 (Chromogenix-Instrumentation Laboratory SpA, Milano, Italy) and substrates for FXa, such as BIOPHEN CS-11 (22) (Aniara, Mason Ohio, USA). Other manual and/or visual forms of coagulation detection may also be implemented.

Other embodiments include the use of fluorogenic substrates, that upon cleavage by an amidolytic enzyme (e.g. thrombin, or factor Xa) release a fluorogenic marker. These embodiments include but are not limited to peptide-4-methylcoumarin amides (MCA), e.g. Pefafluor Fxa (Pefa-5534) (Pentapharm Ltd. Basel, Switzerland) which is a sensitive substrate for 10 factor Xa. In other embodiments, luminogenic substrates are used, these include the substrate S-2613 (t-butyloxycarbonyl-isoleucyl-glutamyl-gamma-piperidyl-glycyl-arginyl-isolu-minol), for other substrates, see e.g. Hemker H. C., Handbook of synthetic substrates for the coagulation and fibrinolytic 15 system, Martinus Nijhoff Publishers, Boston (1983).

In an embodiment, the method further includes the step of adjusting a dose of anticoagulant drug to reach a recommended therapeutic INR of a predefined target, by either increasing the dose to maximize an antithrombotic effect of the anticoagulant drug or decreasing the dose to minimize risk of abnormal bleeding caused by over-anticoagulation.

Kits of the Present Disclosure

In another aspect, the present disclosure provides one or more kits suitable for monitoring anticoagulant therapy in various clinical laboratories and point-of-care testing. Accordingly, the kits are configured to provide, in suitable amount(s) and ready-to-use containers, the necessary reagents for running tests according to the disclosed method. The test kit comprises, e.g., in separate containers, a coagulation reagent, such as one or more of the above mentioned in the description of the methods of the disclosure, and a normal plasma that is deficient in only factors II, IX and X (i.e., factor-deficient plasma), or a mixture of coagulation reagent and factor-deficient plasma in a single container, or a solution containing purified factor VII in a concentration sufficient to provide the mix with a final activity of over 50% (>0.5 u/mL).

The factor-deficient plasma is plasma that is deficient only in factors II, X and IX, such that it still contains other coagulation factors, including factor VII. The factor-deficient plasma is suitably produced as described above, i.e., normal plasma is adsorbed, e.g., with barium sulphate or other suitable adsorbing agent that removes factors II, VII, IX, and X, and factor VII is then added back to the adsorbed plasma in a concentration sufficient to provide over 50% factor VII activity in the final mixture of a test sample and deficient plasma mixture. In an embodiment, the factor-deficient plasma is artificially prepared and produced by immunodepleting methods. In other words, the kit comprises a coagulation reagent and a factor-deficient plasma deficient in vitamin K dependent factors II, IX and X, wherein the factor-deficient plasma includes enough factor VII to provide in the reaction mix at least 0.50 u/mL (50% activity or 0.25 µg/mL) final concentration of factor VII.

In some embodiments, the kits of the disclosure further comprise a calcium ion source, which can be provided in its own designated container or included with the coagulation reagent or the deficient plasma. In other embodiments, calcium is not provided as part of the kit, as many laboratories and coagulation apparatuses have suitable sources of calcium reagent. Calcium need not be added when the test sample is whole blood, e.g., fresh un-anticoagulated blood, such as in point-of-care testing.

In certain embodiments, particularly related to point-of-care testing, the coagulation reagent and the deficient plasma, or purified factor VII, can be provided in one single container or on the surface of a reagent strip or reagent well, which can further be provided with or without calcium ions. In other embodiments the coagulation reagent and deficient plasma are provided in separate containers.

The coagulation reagent and deficient plasma are preferably provided in lyophilized powder form, whether or not these are provided separate or combined in the same vial. The one or more containers are suitably configured so the lyophilized material can be reconstituted in the original container.

The following Examples are presented to further illustrate to persons skilled in the art how to make and use the disclosure. These Examples are not intended as limitations, however, upon the scope of the disclosure.

Example I

In general, the present disclosure provides a solution for monitoring anticoagulant therapy with a reagent plasma composed of a plasma that has been made deficient in all vitamin K dependent factors and subsequently reintroduced with a solution containing factor VII in sufficient quantity to correct the final concentration of factor VII in the reagent-test whole blood or plasma sample mixture. The resulting sample mixture remains deficient in only factors II, X and IX so that the influence of reduced factor VII in the test blood or plasma sample on clotting is eliminated when a coagulation reagent (e.g., thromboplastin or other reagents that directly activates coagulation factor X and do not activate factor IX) is used to initiate the clotting reaction. Example 1 describes a solution for bypassing activation of factor IX and correct factor VII to measure the simultaneous influence of factors II and X on the clotting process.

The present disclosure relates to the concept of mixing a test plasma sample to be tested with plasma that is deficient (i.e., totally depleted) in factors II, X, and IX to thereby correct for other possible coagulation factor deficiencies in the test sample, and subsequently measuring clotting time following activation of coagulation with a coagulation reagent that activates coagulation factor X directly or in complex with factor VIIa (i.e., thromboplastin/tissue factor). As such, the ensuing test results only reflect the activity of coagulation factors II and X.

The test can be measured by manual pipetting or in semi-automatic and automatic coagulation instruments. Using the disclosed method, which is sensitive to reduced factors II and X only, compared to existing methods, which are sensitive to reduced factors II, VII and X in measuring the prothrombin time (PT), provides optimal results. The PT is sensitive to reduced factor VII as well as factors II and X in test samples. Factor VII fluctuates, due to short half-life, out of synchrony compared to factors II and X, and factor VII may be very low when factors II or X are not. Such fluctuations can influence tests results and dose management when using traditional PT methods; however, the disclosed method and kit bypass activation of factor IX, correct any influence of factor VII, and accurately measure the simultaneous influence of factors II and X only on the clotting process, i.e., the influence of the two coagulation factors that bring about the antithrombotic effect of vitamin K antagonists.

The test results may be obtained and recorded as a clotting time, clotting time ratio, or another calculation. The experimental results demonstrated in the present example are based on measuring clotting times e.g., with thromboplastin and with a modified reagent (i.e., thromboplastin/adsorbed plasma mixture) as the coagulation reagent. Purified factor VII obtained is then mixed in.

A test plasma sample (patient plasma) is mixed with a factor-deficient plasma. The factor-deficient plasma is a normal plasma that has been adsorbed, e.g., with barium sulphate or other suitable adsorbing agent that removes factors II, VII, IX and X, and subsequently combined with factor VII in a concentration sufficient to provide over 50% factor VII activity in the final mixture of test sample and deficient plasma mixture. Using such mixture, by adding thromboplastin and calcium to initiate the measured reaction, a clotting time can be measured that is only sensitive to reductions in factors II and X. Based on the resulting clotting time, the proportions of test plasma to the factor-deficient plasma can be in the range from 1:1 to 1:20 parts, preferably in the range from 1:2 to 1:5 (see below). Alternatively, factor deficient plasma and purified factor VII are mixed into thromboplastin or purified factor VII is mixed into the thromboplastin/adsorbed plasma mixture.

In the experimental results of Example I, the method mixes 10 uL test plasma with 25 µL of the factor-deficient plasma. The factor-deficient plasma contains at least 0.8 u/mL of factor VII and is deficient in factors II, IX and X. The ratio of test plasma to the factor-deficient plasma is 1:2.5, which provides >0.5 u/mL final concentration of FVII in the mixture. Subsequently, 70 uL Owren's buffer solution (e.g., composed of sodium diethyl-barbiturate, sodium chloride, hydrochloric acid, and distilled water) having a pH of approximately 7.33, is mixed in to make a total volume of 105 uL before adding thromboplastin and calcium to measure the clotting time.

The resulting measurements are used to reliably and specifically measure reduced factors II and X concentrations with no interference from factor VII that is over 0.5 u/mL in the mixture. To accurately measure factors II and X concentrations as low as <2 u/dL, a preferred ratio of test plasma to factor-deficient plasma is in the range of 1:2 to 1:10.

Example II

Example II describes a comparison of mixing test blood or plasma with a former testing method (using double immunodepleted factor II and factor X only deficient plasma) described in U.S. Pat. No. 9,234,902 ("the '902 patent"), filed on Mar. 7, 2012, by Fiix Diagnostics, and published on Jan. 12, 2016, against the disclosed method (using adsorbed plasma spiked with FVII) before adding thromboplastin.

The plasma reagent disclosed in the '902 patent includes FII and FX double immunodepleted plasma method before adding thromboplastin and calcium chloride. In the former testing method, the aim was to achieve a measurement of the simultaneous influence of reduced FII and FX only during warfarin monitoring. This was achieved by mixing FII and FX double immunodepleted plasma to the citrated test plasma sample before adding thromboplastin and calcium chloride. In this manner the test plasma was corrected for all factor deficiencies other than that of FII and FX, resulting in a clotting time that only reflected reductions in FII and FX. However, the double immunodepletion of the plasma reagent has been proven to be a slow and expensive manufacturing method.

The method of present disclosure achieves the goal of simultaneously measuring only the effect of reduced FII and/or FX by replacing the double immunodepleted plasma with barium sulphate adsorbed (or adsorbed by other method) plasma that has been spiked with surplus FVII while remaining deficient in FII, FX and FIX. The spiked concentration of FVII preferably provides a factor activity of over 50% in the test plasma/spiked reagent plasma mixture. The reagent plasma remains deficient in FIX as well; however, measuring such is immaterial because the thromboplastin activates FVII and bypasses FIX. Therefore, this test is only affected by reductions in FII and/or FX.

FIG. 1 illustrates the effect of adding FVII to test plasma prior to adding thromboplastin. Normalized ratios were calculated with different thromboplastin reagents in plasma samples with progressively increasing FVII concentrations (from 0.0-0.7 µg/ml=0-140% FVII activity). Mean normal FVII concentration is approximately 0.5 µg/ml=100% activity. FIG. 1 shows that whereas the PT-INR is affected by low factor VII, the other test configurations successfully eliminated the influence of low FVII activity.

Reagents used include a control test (PT INR) with no FVII addition to test plasma), test plasma spiked with purified FVII (94% FVII added activity in final test sample with reagent mix; i.e., FVII activity is not less than 94%), disclosed method (FVII spiked adsorbed plasma with FVII mixed into test plasma (>65% final activity), having thromboplastin added separately), and the former testing method (double immunodepleted FII and FX deficient plasma with FVII activity about 100% mixed into test plasma (>50% final activity), having thromboplastin added separately).

Results showed that only the standard control test was influenced by FVII concentrations less than about 0.4 microg/ml (<80%). All the other plasma reagent methods corrected the test sample for any degree of FVII deficiency and, therefore, are independent of test sample FVII activity and, hence, suitable for simultaneous factor II and X activity detection. Example II supports the finding that the presently disclosed solution achieves results similar (i.e., bioequivalent) to the former testing method while introducing a faster and more cost-effective manufacturable method.

Example III

Figure 2:
FIG. 2 is a graph illustrating the effect of purified FVII spiked thromboplastin on pooled normal plasma and FVII deficient plasma.

Example III supports an alternative embodiment of the disclosed method and describes the effect of spiking the thromboplastin (as opposed to spiking the test plasma) with purified FVII. FIG. 2 illustrates this effect of purified FVII spiked thromboplastin on pooled normal plasma and FVII deficient plasma. Thromboplastin or thromboplastin spiked with purified factor VII (pFVII) was added to pooled normal plasma (PNP, about 100% FVII) and FVII deficient plasma (0% FVII). The thromboplastin was spiked with two pFVII concentrations to obtain an added FVII final activity of no less than 93-186% in test plasma-thromboplastin mixtures.

Results obtained per FIG. 2 demonstrated that purified FVII spiked thromboplastin corrected the clotting times if FVII deficient plasma was normal. In other words, the thromboplastin mixed with purified FVII (providing at least 93% FVII in the final mixture) successfully eliminated the influence of low FVII concentrations in test plasma on the clotting time.

Figure 3:
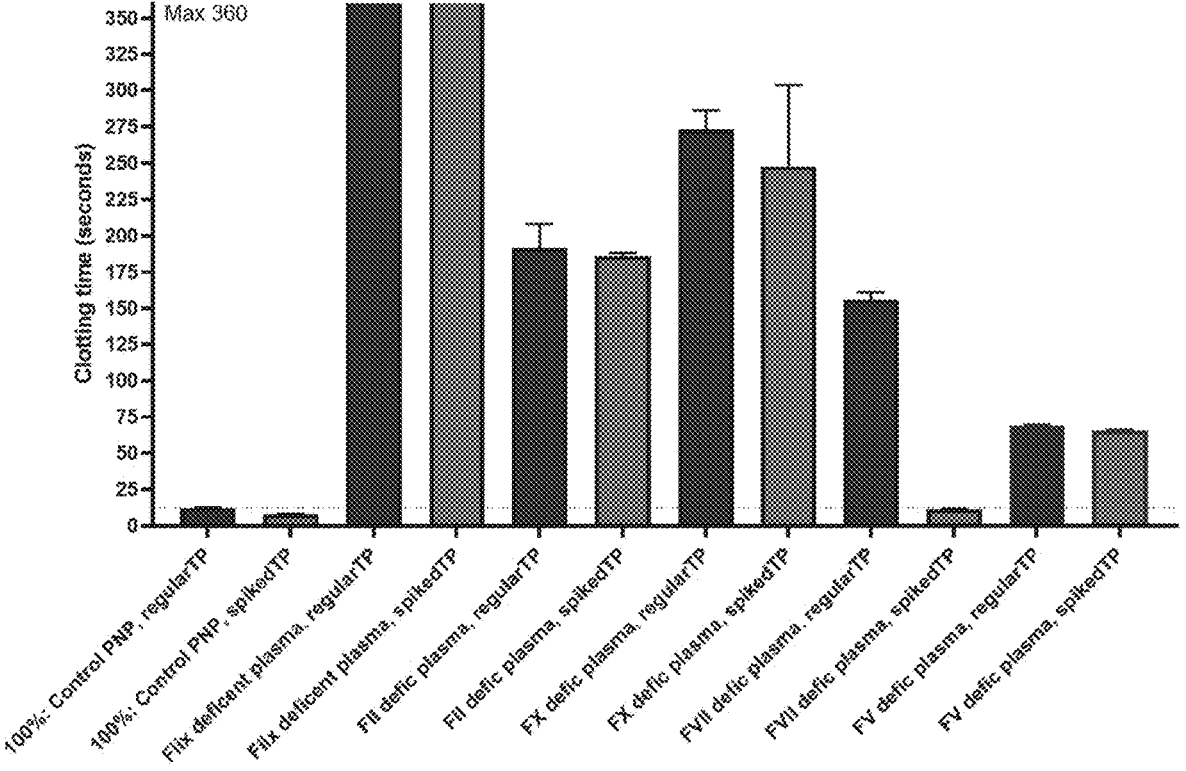
FIG. 3 is a graph illustrating the effect of purified FVII spiked thromboplastin on different deficient plasmas.

FIG. 3 illustrates the effect of purified FVII spiked thromboplastin on different plasmas. The experiment tests the influence of a control thromboplastin (i.e., conventional thromboplastin) and purified FVII spiked thromboplastin on clotting times in pooled normal plasma, Fiix-deficient adsorbed plasma spiked with 65% FVII), and in immunodepleted plasmas: FII deficient plasma, FX deficient plasma, FVII deficient plasma and FV deficient plasma).

Results obtained as per FIG. 3 further demonstrated that purified FVII spiked thromboplastin to yield at least 93% final activity has no or minimal influence on clotting times in pooled normal plasma, FII and FX deficient plasma, or FV deficient plasma. However, the purified FVII spiked thromboplastin corrects FVII deficient plasma clotting time to normal and therefore clotting time becomes independent of FVII concentration in test plasmas.

Example IV

Example IV describes the sensitivity of the PT Owren's test sample thromboplastin mixed adsorbed plasma (diluted and undiluted test samples); conventional PT Quick thromboplastin; Fiix adsorbed plasma spiked with purified FVII; Fiix purified FVII spiked thromboplastin mixed adsorbed plasma (diluted and undiluted samples); and Fiix purified FVII spiked thromboplastin (i.e., Fiix common pathway test). In the experiments, the Quick PT included a thromboplastin. The Fiix PT with FVII spiked reagent included a thromboplastin with surplus purified FVII, referred to as a "common pathway test" and is sensitive to reduced FI, FII, FV, and FX. The Owren's PT included thromboplastin reagent Simplastin A (i.e., SPA thromboplastin) having adsorbed plasma mixed in with the thromboplastin as source of fibrinogen and factor V, testing such included using both undiluted plasma and 1:7 plasma dilution in Owren's buffer. The Fiix PT with purified FVII spiked reagent included surplus purified factor VII, undiluted plasma, and 1:7 plasma dilution in a buffer solution composed of sodium diethylbarbiturate, sodium chloride, hydrochloric acid, and distilled water (i.e., spiked thromboplastin with adsorbed plasma FII-FX test). The disclosed method also included adsorbed plasma with added FVII plasma reagent, wherein the thromboplastin was added separately.

Figure 4:
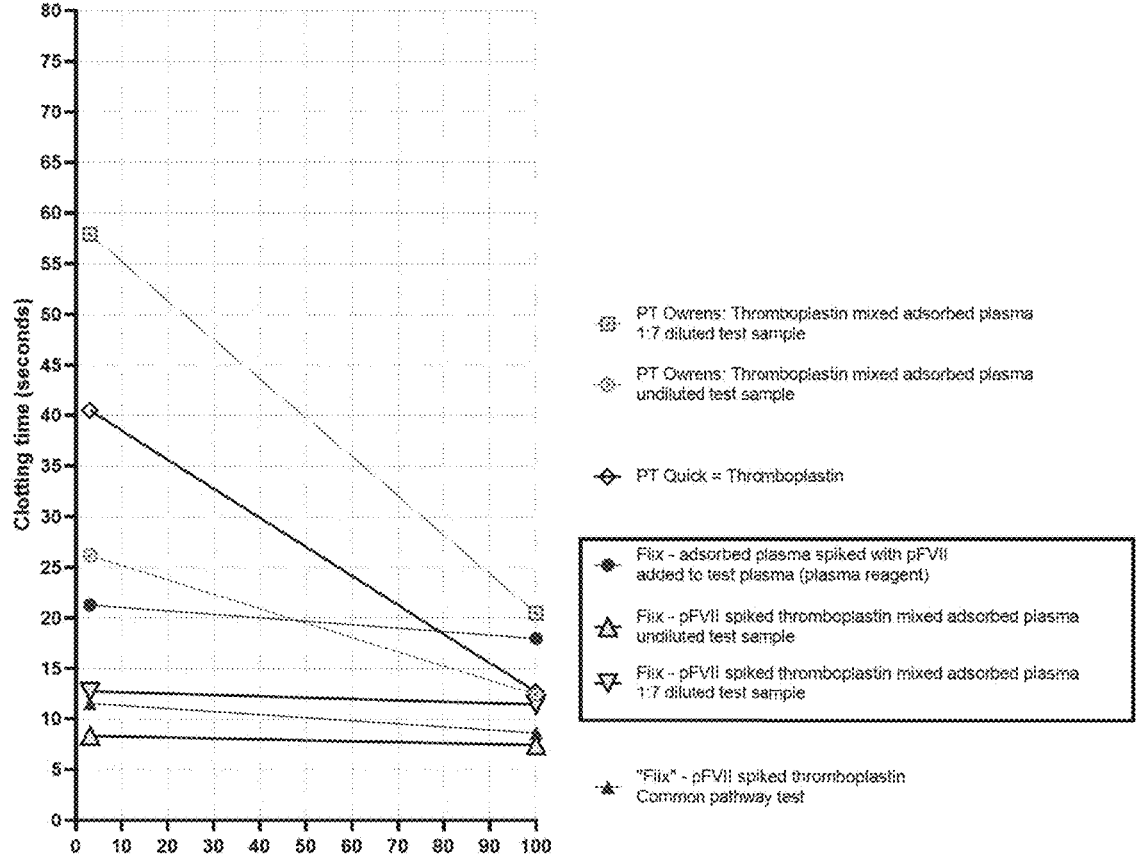
FIG. 4 is a graph illustrating the influence of FVII deficiency PT-INR and alternative variants of the present disclosure.

FIG. 4 illustrates the clotting times in a pooled normal plasma (100%=1.0 u/ml) and plasma with 3% (0.03 u/ml) FVII activity. As observed, all Fiix-test methods (including the former testing method and method from the present disclosure) successfully eliminated the influence of FVII on the clotting times, i.e., clotting times similar in PNP and 3% FVII deficient plasma.

The disclosed Fiix-NR (normalized ratio) method measured in undiluted Fiix test sample with modified reagent (i.e., thromboplastin/adsorbed plasma mixture) spiked with purified factor VII (pFVII) that resulted in no clotting time difference. Example IV suggests that the test can be done on whole blood and could be applicable to point of care testing. Thus, a test method using spiked pFVII with a modified reagent (i.e., including thromboplastin and bovine adsorbed plasma in the proportion of 1:1) test is further contemplated by the disclosure and may be used for a whole blood-based point of care assay.

In an alternative embodiment, the disclosed method and/ or kit includes an adsorbed plasma spiked with purified FVII mixed into test blood or plasma before adding thromboplastin and calcium chloride. The solution includes 1 part (25 µL) test plasma and 1 part (25 µL) modified buffer (e.g., Owren-Koller buffer) spiked with purified FVII to make a concentration of 0.7 µg/ml. In the two-part mix there is 0.35 µg/ml f.c. of added pFVII (=70% added activity). In other words, FVII activity in the test plasma dilution will be over 70%. Alternative configurations could include FVII activity as low as 50%. Following the creation of the two-part mix, four parts (100 µL) thromboplastin (e.g., Quick type) and calcium chloride are added, and clotting time is subsequently measured. Alternative configurations could include FVII activity as low as 50% and a different volume of pFVII spiked buffer.

In an alternative embodiment, the disclosed method and/ or kit includes a purified FVII spiked modified (thromboplastin-based) reagent, wherein the modified reagent includes thromboplastin and bovine adsorbed plasma in a 1:1 ratio. The modified reagent spiked with purified FVII and calcium chloride is first added to the test blood or plasma. The solution includes 1 part (50 µL) undiluted test plasma and 2 parts (100 µL) modified reagent spiked with purified FVII 0.7 µg/ml f.c. (140% activity). In the mixture there is 93% FVII activity. Alternative configurations could use as little as 0.4 µg/ml f.c (80% activity) purified FVII in the spiked buffer to obtain over 50% final activity in the test plasma-thromboplastin mix. In an embodiment, the modified reagent is a mix of thromboplastin and barium sulphate adsorbed plasma that serves as a correcting source to the test plasma of all coagulation factors other than the vitamin K dependent factor (II, VII, IX and X). By spiking the reagent with purified FVII and triggering coagulation with thromboplastin, the test is sensitive only to reductions in FII and FX.

It is understood that not all objects or advantages may be achieved under any embodiment of the disclosure. Those skilled in the art will recognize that the proposed method and kits for monitoring anticoagulant therapy may be embodied or carried out to achieve or optimizes one advantage or group of advantages as taught herein without achieving other objects or advantages as taught or suggested herein.

Those skilled in the art will recognize the interchangeability of various disclosed features. Besides the variations described herein, other known equivalents for each feature can be mixed and matched by one of ordinary skill in this art to build and use an alternative plasma reagent under principles of the present disclosure. The skilled artisan will understand that the features described herein may be adapted to other methods and types of diagnostic devices/applications.

It is intended that the present disclosure should not be limited by the disclosed embodiments and examples described above and may be extended to other applications that may employ the features described herein.

The invention claimed is:

1. A method for measuring and monitoring a combined effect of an anticoagulant drug on coagulation factors II and X in a patient taking the anticoagulant drug, the method comprising:

obtaining a test sample from the patient;

mixing factor VII into one or more coagulation reagents that activate factor X through factor VII and bypasses factor IX;

adding the one or more coagulation reagents with the factor VII to the test sample; and determining blood clotability of the test sample by measuring an influence of factors II and X.

2. The method of claim 1, wherein the one or more coagulation reagents include thromboplastin.

3. The method of claim 1, wherein the test sample is plasma obtained from the patient.

4. The method of claim 3, wherein the one or more coagulation reagents are pre-mixed with a calcium reagent and with factor VII.

5. The method of claim 1, wherein the factor VII is provided as purified factor VII.

6. The method of claim 1, wherein the test sample is un-anticoagulated whole blood.

7. The method of claim 1 further comprising the step of adjusting a dose of anticoagulant drug to reach a recommended therapeutic international normalized ratio (INR) of a predefined target, by either increasing the dose to maximize an antithrombotic effect of the anticoagulant drug or decreasing the dose to minimize risk of abnormal bleeding caused by over-anticoagulation.

8. The method of claim 1, wherein the anticoagulant drug is an oral anticoagulant.

9. The method of claim 1 further comprising the step of diluting the test sample with buffer or saline solution.

10. The method of claim 1, wherein the one or more coagulation reagents are diluted with water, a saline aqueous solution or buffered aqueous solution.

11. The method of claim 1, wherein at least one component of the one or more coagulation reagents is lyophilized, and wherein the method further comprises a step of reconstituting the at least one component.

* * * * *